US007175830B2

(12) United States Patent
Collins et al.

(10) Patent No.: US 7,175,830 B2
(45) Date of Patent: Feb. 13, 2007

(54) IMAGING OF DRUG ACCUMULATION AS A GUIDE TO ANTITUMOR THERAPY

(75) Inventors: Jerry M. Collins, Rockville, MD (US); Raymond W. Klecker, Jr., Silver Spring, MD (US); Lawrence W. Anderson, Wheaton, MD (US)

(73) Assignee: The United States of America as represented by the Secretary of Health and Human Services, Washington, DC (US)

( * ) Notice: Subject to any disclaimer, the term of this patent is extended or adjusted under 35 U.S.C. 154(b) by 224 days.

(21) Appl. No.: 10/319,812

(22) Filed: Dec. 16, 2002

(65) Prior Publication Data

US 2003/0198594 A1 Oct. 23, 2003

Related U.S. Application Data

(63) Continuation-in-part of application No. 10/088,561, filed as application No. PCT/US00/25833 on Sep. 21, 2000.

(60) Provisional application No. 60/155,061, filed on Sep. 21, 1999.

(51) Int. Cl.
  *A61K 49/04* (2006.01)
(52) U.S. Cl. ............... 424/9.4; 424/1.11; 424/1.65; 424/1.81; 424/9.1; 424/9.2
(58) Field of Classification Search ............. 424/1.11, 424/1.65, 1.81, 1.85, 9.1, 9.4, 9.2; 546/1, 546/152, 184
See application file for complete search history.

(56) References Cited

U.S. PATENT DOCUMENTS 5,981,564 A 11/1999 Pagé et al.
6,441,025 B2 8/2002 Li et al.

FOREIGN PATENT DOCUMENTS

WO   WO 92 19264   11/1992

OTHER PUBLICATIONS

Takimato et al, Cancer Chemotherapy and Biotherapy, 2nd Edition, p. 463, Lippincott-Raven, Philadelphia, 1996.*
Thomas et al. (Bioorg. Med. Chem., 12 (2004) 1585-1604).*
Pizzolato et al (The Lancet, 2003, vol. 361, pp. 2235-2242).*
Levchenko, A., et al., "Evaluation of 11C-Colchicine for PET Imaging of Multiple Drug Resistance," *Journal of Nuclear Medicine*, vol. 41, No. 3, pp. 493-501 (Mar. 2000).

Inoue, Tomio, et al., "Preliminary Study Of Cardiac Accumulation Of F-18 Fluorotamoxifen In patients With Breast Cancer," *Clinical Imaging*, vol. 21, pp. 332-336 (1997).
Shields, Anthony F., et al., "Carbon-11-Thymidine and FDG to Measure Therapy Response," *The Journal of Nuclear Medicine*, Vol. 39, No, 10, pp. 1757-1762 (Oct. 1998).
Kuh, Hyo-Jeong, et al., "Determinants of Paclitaxel Penetration and Accumulation in Human Solid Tumor," *Journal of Pharmacology and Experimental Therapeutics*, vol. 290, No. 2, pp. 871-880 (1999).
Schirbel, Anreas, "Synthesis of n.c.a. PET-radiotracers with carbon-11," *Berichte des Forschungszentrums Jülich*, 3602, pp. 1-110 (1998).
Kangas, Lauri, et al., "Biodistribtution and Scintigraphy of C-Toremifene in Rats Bearing DMBA-Induced Mammary Carcinoma," *Pharmacology & Toxicology*, vol. 64, pp. 373-377 (1989).
Hendrikse, N. Harry, et al., "A New *in Vitro* Method to Study P-Glycoprotein Transport in Tumors and The Blood-Brain Barrier," *Cancer Research*, vol. 59, pp. 2411-1426 (May 15, 1999).
Josien, Hubert, et al., "A General Synthetic Approach to the (20S)-Camptothecin Family of Antitumor Agents by a Regiocontrolled Cascade Radical Cyclization of Aryl Isonitriles," *Chem.—Eur. J.*, vol. 4(1), pp. 67-83 (1998).
Rao, Ch. Srinivasa, et al., "Synthesis and Evaluation of [$^{14}$C]-Labelled and Fluorescent-Tagged Paclitaxel Derivatives as New Biological Probes," *Bioorganic & Medicinal Chemistry*, vol. 6, pp. 2193-2204 (1998).
Penco, Sergio, et al., "Synthesis of [14-$^{14}$C] Daunorubicin and Doxorubicin," *Journal of Antibiotics*, vol. XXX, No. 9 (Sep. 1977).

* cited by examiner

*Primary Examiner*—Dameron L. Jones
(74) *Attorney, Agent, or Firm*—Venable LLP; Thomas G. Wiseman; Keith G. Haddaway

(57) ABSTRACT

The use of radio-labeled antitumor drugs in the treatment of solid tumors by the method of administering a radio-labeled anticancer drug to a patient and imaging at least a part of the patient using Positron Emission Tomography imaging is described. The method can be used to monitor delivery of antitumor drugs to tumors, to predict the effectiveness of therapy with a particular antitumor drug or combination of antitumor drugs, to assess the effectiveness of modulators of cellular accumulation, to individualize therapy and to evaluate the effectiveness of antitumor drugs with respect to particular cancers. Particularly preferred drugs are labeled taxanes, e.g., $^{11}$C-paclitaxel and $^{11}$C-docetaxel, labeled anthracyclines, e.g., $^{11}$C-doxorubicin and $^{11}$C-epirubicin, and other radiolabeled drugs, e.g. $^{11}$C-topotecan, $^{11}$C-SN-38, and $^{11}$C-imatinib. The invention further describes antitumor drugs labeled with the radioactive label $^{11}$C and methods of preparing radio-labeled drugs.

23 Claims, No Drawings

IMAGING OF DRUG ACCUMULATION AS A GUIDE TO ANTITUMOR THERAPY

CROSS REFERENCE TO RELATED APPLICATIONS

This application is a continuation-in-part of application Ser. No. 10/088,561, filed Mar. 19, 2002, which is a 371 of PCT/US00/25833, filed Sep. 21, 2000 which claims the benefit under 35 U.S.C. 119(e) of U.S. provisional application No. 60/155,061, filed Sep. 21, 1999.

FIELD OF THE INVENTION

The present invention relates to the use of radio-labeled antitumor drugs in the diagnosis and treatment of cancers characterized by solid tumors. The invention also relates to radio-labeled antitumor drugs and their preparation.

Cancer treatment has made great progress in recent years. Many new therapies are becoming available, and many more patients are treated. Cancer is characterized by unrestricted cell growth; many cancer therapies work by inhibiting cell division. Since normal cells do not divide after maturation, inhibition of cell division primarily affects the cancer cells and this has been a focus of drug development. However, other cells are also affected by antitumor drugs to different degrees and cancer therapies are often extremely toxic to patients. There is also great variability in the efficacy of treatments. Some drugs are more effective than others for certain patients, for certain cancers, or at certain stages of treatment. Often, combinations of drugs with varying dosages are necessary for efficacious treatment, requiring considerable experimentation to optimize drugs and doses.

Among the agents affecting the therapeutic benefits of cancer drugs are the multi-drug resistance transporter (MDR), also called p-glycoprotein (PGP) or ABCB1. It has recently become clear that MDR is one of a family of such transporters. Klein I, Sarkadi B, Varadi A. An inventory of the human ABC proteins. *Biochim. Biophys. Acta* 1999; 1461:237–62. The expression of these proteins can be highly variable. MDR is not expressed in all cancer cells, and may be present at variable levels. The expression of MDR affects drug efficacy by altering drug accumulation at the tumor. Because of the variable efficacy of antitumor drugs caused by this and other factors, a critical part of therapeutic monitoring involves determining the drug location in the body, its half-life, and the range of mechanisms that limit its effectiveness.

Accumulation of a drug reflects the net balance over time of influx (delivery to the tumor) and efflux (removal from the tumor). Influx and efflux are equally important, but recent research has focused upon a series of transport proteins that function as efflux pumps for taxanes, anthracyclines, and other drugs. There are many reasons why a tumor may not be sensitive to a particular drug. However, the first parameter to evaluate is accumulation of drug by the tumor. If the drug doesn't accumulate in the tumor, there won't be an effect. Adequate accumulation is always necessary for drug activity. Thus, a method to determine accumulation of a drug in the tumor could be the first step in therapeutic decision-making for the drug.

Traditional approaches to the determination of drug uptake and retention (drug accumulation in the tumor) have been invasive and most frequently require obtaining a biopsy from the patient. In addition to the discomfort and risks associated with biopsy procedures, only a small sample of tissue is typically obtained, which may not be representative of the entire region.

Taxanes

One class of drugs which has proved particularly useful in the treatment of cancer, including solid tumors such as breast cancer, has been the taxanes. Taxanes are diterpenoid compounds with a complex taxane ring as the nucleus. The taxane paclitaxel (I) (Taxol®) was initially isolated from yew bark, although the compound may now be prepared synthetically. A modification of the side chains of paclitaxel has yielded another clinically effective compound, docetaxel (II). Other taxanes have also been developed, and are at various stages of preclinical and early clinical testing. These analogs include differences in functional groups attached to the main baccatin nucleus, as well as different side chains attached at the C-13 position.

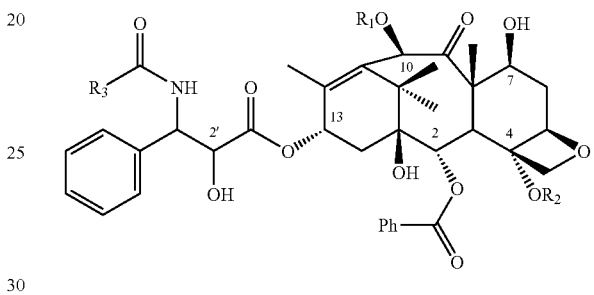

(I) Paclitaxel: $R_1=R_2$=acetate, $R_3$=Ph
(II) Docetaxel: $R_1$=OH, $R_2$=acetate, $R_3$=OC(CH$_3$)$_3$ Taxanes, like the vinca alkaloids and colchicine, work by interfering with microtubules, thereby inhibiting mitosis. Taxanes antagonize disassembly of microtubules, by promoting tubulin polymerization and inducing microtubule bundles to form. This leads to arrest of mitosis, and ultimately to cell death. The rate of cell death is proportional to the concentration of drug and the length of time of administration. Taxanes are highly insoluble and are commonly administered in a solution of surfactants and other vehicles such as ethanol. (Hardman, J. G. and Limbird, L. E.,(eds) *Goodman and Gilman's The Pharmacological Basis of Therapeutics*, Chapter 51, McGraw-Hill, N.Y., 1996)

The taxane class of anticancer drugs has demonstrated remarkable activity. Docetaxel and paclitaxel, the first two approved drugs in this class, have already altered the standard treatments for breast, lung, and ovarian tumors. Crown J, O'Leary M. The taxanes: an update. *Lancet* 2000; 355 (9210):1176-8. Burris H A 3rd. Docetaxel (Taxotere) in the treatment of cancer. *Semin. Oncol.* 2000; 27 (2 Suppl 3):1-2. The full scope of antitumor activity for docetaxel and paclitaxel is still under active investigation, with new uses emerging for other tumor types. For example, at present there is considerable interest in the use of docetaxel for treatment of prostate cancer. Oh W K, et al. Docetaxel (Taxotere)-based chemotherapy for hormone-refractory and locally advanced prostate cancer. *Semin. Oncol.* 1999; 26 (5 Suppl 17):49–54; Petrylak D P. Docetaxel (Taxotere) in hormone-refractory prostate cancer. *Semin. Oncol.* 2000; 27 (2 Suppl 3):24–9. Other molecules in the taxane class are at much earlier stages of clinical testing.

Anthracyclines

Anthracyclines represent another important class of antitumor drugs. Representative anthracycline drugs include doxorubicin (III) and epirubicin (IV). These anthracyclines are leading agents for the treatment of many tumors, notably breast cancer, lung cancer, and sarcomas. Doroshow J H. Anthracylines and anthracenediones. In: Chabner B A and Longo D L, *Cancer Chemotherapy and Biotherapy*, 2<sup>nd</sup> Edition, p. 409, Lippincott-Raven, Philadelphia, 1996. Several mechanisms of action have been proposed, based upon the intercalation of the anthracycline molecules with DNA and subsequent disruptions of cellular functioning.

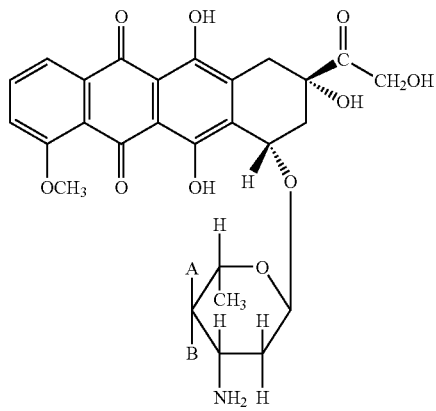

(III) Doxorubicin: A=H; B=OH
(IV) Epirubicin: A=OH; B=H

Other Antitumor Drugs

Because the discovery of anticancer drugs has been well-funded over the last half-century, drugs from a variety of chemical classes are now in routine clinical use. Mitoxantrone (V) is an anthracenedione, a chemical class closely related to anthracyclines. Mitoxantrone was originally developed in an attempt to replace anthracyclines because the anthracenediones have lower cardiac toxicity. However, the antitumor activity of mitoxantrone was generally disappointing and it has a relatively narrow niche in clinical use. Recently, however, mitoxantrone has been demonstrated to substantially reduce the severe pain associated with metastatic prostate cancer, and has changed the management of this large group of cancer patients. Tannock I F, Osoba D, Stockler M R, Ernst D S, Neville A J, Moore M J, Armitage G R, Wilson J J, Venner P M, Coppin C M, Murphy K C. Chemotherapy with mitoxantrone plus prednisone or prednisone alone for symptomatic hormone-resistant prostate cancer: a Canadian randomized trial with palliative end points. *J. Clin. Oncol.* 1996; 14(6): 1756–64.

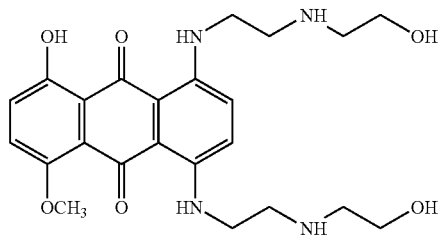

(V) Mitoxantrone

Camptothecin (VI) is a natural product found in the bark and wood of a Chinese tree.

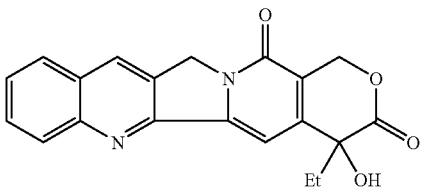

(VI) Camptothecin

Although found to be too difficult for clinical use itself, a number of derivatives have demonstrated clinical activity. Takimoto C H, Arbuck S G. The Camptothecins. In: Chabner B A and Longo D L, *Cancer Chemotherapy and Biotherapy*, 2<sup>nd</sup> Edition, p. 463, Lippincott-Raven, Philadelphia, 1996. This class of drugs appears to work by inhibiting the action of topoisomerase I, a key enzyme for the integrity of DNA structure. Irinotecan (CPT-11) (VII) was initially approved for treatment of colorectal cancer, and topotecan (VIII) initially approved for ovarian cancer. Both of these two drugs and other camptothecin analogs are acquiring new uses as testing continues.

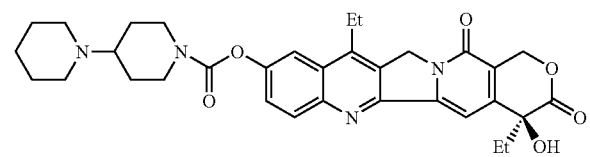

(VII) Irinotecan

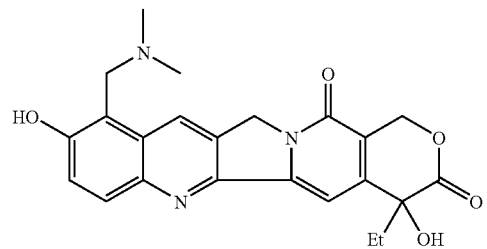

(VIII) Topotecan

Irinotecan itself shows only modest antitumor activity. Furthermore, it circulates in the body at concentrations about 100-fold higher than that of its metabolite, SN-38 (7-ethyl-10-hydroxycamptothecin) (IX), which is the active form. Thus, imaging approaches should focus upon SN-38 rather than irinotecan.

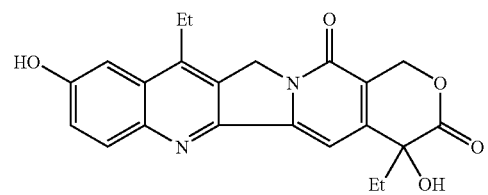

(IX) SN-38

Topotecan has shown activity in lung cancer, and is now also approved for treating these patients. In addition, topotecan is particularly important from the perspective of PET imaging because it is direct-acting, and also has limited catabolism, so that the parent molecule is the principal circulating species.

Imatinib (Glevec®; ST1571) (X) has been a very high profile anticancer drug over the last few years. It was first approved for marketing in the United States in May 2001 for treatment of chronic myelogenous leukemia (CML), and subsequently in January 2002 for treatment of gastrointestinal stromal tumors (GIST). Use of imatinib as sole therapy is not curative, so the current emphasis is upon developing combinations of imatinib with other chemotherapeutic drugs. This drug is currently being tested for other solid tumors, including for tumors located in the brain.

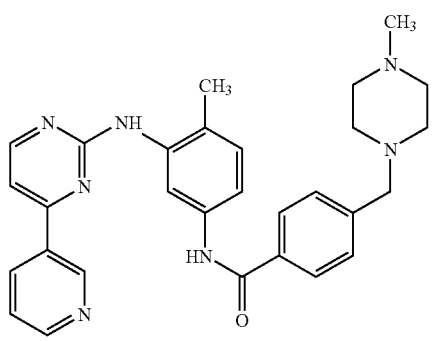

(X) Imatinib

Determination of Sensitivity or Resistance

Although drugs having excellent antitumor activity, e.g., taxanes, anthracyclines and others, have been identified, not all tumors respond to a given therapy. Furthermore, all patients are exposed to the risk of severe, life-threatening toxicity with these drugs whether or not their tumors respond. An important tool for individualizing therapy would be a method to rapidly determine whether a specific tumor will be likely to respond to a particular drug without exposing the patient to toxic levels of the drug.

In addition to avoiding needless toxicity, a rapid determination is also important because of the tendency of tumors to become more difficult to treat with time. Thus, if one treatment can be predicted to be unsuitable, alternative treatments can be explored without waiting months to determine that the first treatment did not work.

In some cases, the cause of treatment failure can not be determined. In other cases, a specific biochemical or molecular mechanism can be ascertained. For example, the tumor cells may be intrinsically sensitive to the drug, but inadequate amounts of drug are accumulated in the tumor. There are multiple reasons for drug accumulation failures, but, regardless of the underlying cause, the empirical demonstration that adequate (or inadequate) drug was accumulated has enormous medical value in terms of treatment selection for individual patients. Determining drug accumulation levels in a specific tumor pre-treatment would thus provide a great value in exploring a wide range of treatment options.

In addition to the benefits for individual patients, determination of drug delivery has benefits for the general patient population and for the process of drug development. General patient populations include a mixture of tumors which are chemosensitive and chemoresistant. The demonstration of a substantial effect is made difficult when the responding tumors are diluted in a pool of nonresponding tumors. Thus, any technique which can find tumors likely to respond before treatment has begun will produce an enriched study population, and greatly decrease the numbers of patients required to test the overall potential benefit of the drug.

Position Emission Tomography (PET) imaging or scanning uses positron emitter labeled tracers. Positrons are positively charged electrons which result from the decay of a proton rich and neutron deficient isotope. These emitters are generally short lived. Most positron emitters are produced in medical cyclotrons or accelerators. The half life of $^{11}$C is 20 minutes and of $^{18}$F is 110 min. PET cameras have a spatial resolution of several millimeters and can be used to image the entire body.

The concept of trying to find radiolabeled probes that would be ideal for the investigation of one or more transport pumps should not be confused with the concept of measuring accumulation of a specific drug to guide therapy. The literature is filled with research that attempts to define drug transport systems. Many groups are attempting to find the "ideal" probe for each transporter. The emerging problem is an explosion in the numbers of transporters that are being discovered. Thus, attempts to guide therapy with a drug based upon ideal probes is fraught with difficulty and confounded by the multiplicity of transport mechanisms, which will vary from tumor-to-tumor.

Clinical attempts to measure drug accumulation with imaging have been reported, including the use of $^{11}$C-verapamil, $^{11}$C-daunorubicin, or $^{99m}$Tc-sesta-MIBI. All have been limited because they only target MDR and have additional difficulties.

Verapamil is known to interact with the MDR efflux pump, and Hendrikse et al. have demonstrated that images can be obtained with $^{11}$C-verapamil in rats. Hendrikse N H, de Vries E G, Eriks-Fluks L, van der Graaf W T, Hospers G A, Willemsen AT, Vaalburg W, Franssen E J. A new in vivo method to study P-glycoprotein transport in tumors and the blood-brain barrier. *Cancer Res.* 1999; 59:2411–6. Their work also showed that modulation of MDR in vivo could be demonstrated in rats with $^{11}$C-verapamil. Although $^{11}$C-verapamil may be an elegant probe for MDR per se, it is neither structurally nor functionally related to any approved anticancer drugs such as the taxanes, anthracyclines, anthracenediones camptothecin, imatinib or their analogs. It is also important to recognize that, in humans, there is rapid and extensive catabolism of verapamil. Schomerus M, Spiegelhalder B, Stieren B, Eichelbaum M. Physiological disposition of verapamil in man. *Cardiovasc. Res.* 1976; 10(5):605–12. Verapamil itself constitutes only a small fraction of the circulating radioactivity, so the interpretation of the total radioactivity signal obtained with PET is problematic.

Also, although daunorubicin has been used as a probe in cell culture, where it is a stable molecule, it is not a stable molecule in the body and imaging with this compound is not very useful. In humans, daunorubicin is converted rapidly by carbonyl reductase to its alcohol metabolite, daunorubicinol. Thus, the signal observed via external PET imaging of labeled daunorubicin is a mixture of these two chemical entities, which can complicate the interpretation. The plasma ratio of metabolite-to-parent is about 2.5:1 (Galettis P, Boutagy J, Ma D D. Daunorubicin pharmacokinetics and the correlation with P-glycoprotein and response in patients with acute leukaemia. *Br. J. Cancer* 1994; 70(2):324–9), so it is possible that the metabolite is the species primarily being imaged. However, it is also possible that tissue uptake is more favorable for the parent, so a different ratio might be found.

$^{99m}$Tc-sesta-MIBI, which is routinely used for cardiac imaging, has also been explored for tumor imaging. As in the case for verapamil, neither the structural nor functional properties of sestamibi resemble those for anticancer drugs. The clinical imaging results are mixed. This probe seems to have the ability to detect tumors and monitor response in some clinical settings. Mankoff D A, Dunnwald L K, Gralow J R, et al. Monitoring the response of patients with locally advanced breast carcinoma to neoadjuvant chemotherapy using $^{99m}$Tc-sestamibi scintimammography. *Cancer* 1999; 85(11):2410–23. It is reported that the efflux rate of $^{99m}$Tc-sesta-MIBI correlates with antitumor response, at least for one stage of breast cancer. Ciarmiello A, Del Vecchio S, Silvestro P, et al. Tumor clearance of technetium 99m-sestamibi as a predictor of response to neoadjuvant chemotherapy for locally advanced breast cancer. *J. Clin. Oncol.* 1998; 16:1677–83. However, in lung cancer, no predictive value was found. Sasaki M, Kuabara Y, Yoshida T, et al. Can 99m-Tc-mibi-SPECT predict the treatment response of lung cancer? *J. Nucl. Med.* 2000; 41:286P.

SUMMARY OF THE INVENTION

The invention provides advantages that were not previously available by providing a non-invasive method for determining potential drug efficacy by measuring actual drug accumulation in tumors. This invention allows for the efficient determination of potentially efficacious treatment plans for antitumor therapy by allowing for individualized optimization of drugs and dosage.

The invention offers the additional, previously unrealized advantage of developing individualized antitumor therapies specific to a particular patient with a particular type of tumor in a particular stage of development.

The invention provides a method for determining the effectiveness of particular drugs as treatment for particular cancers over a broad range of the population.

The invention satisfies a long-felt need for radiolabeled anti-tumor compounds and methods of making such compounds that were previously unobtainable. Methods according to the invention provide compounds for testing in a form that retains sufficient radioactivity to be useful for imaging, particularly PET imaging. The synthetic methods require relatively short reaction times and proceed in sufficient yield to provide sufficient time for synthesis, administration and imaging with time frames sufficient to obtain useful diagnostic and therapeutic information. Because the compounds of the invention are radiolabeled versions of drugs themselves, rather than derivatives or analogues of the drugs, the information obtained is particularly relevant.

Non-invasive, external imaging methods to visualize the location of a drug in the body avoid the need for biopsies and also have the capability of scanning large areas of the body, indeed, the entire body if necessary.

Since a drug is only effective if it reaches the desired site of action, a method to determine the location of the drug after administration allows monitoring of the potential effectiveness of drug administration. Antitumor drugs in particular are often toxic, and monitoring could reduce the time required to find the most effective and targeted therapy. Administration of a radio-labeled antitumor drug (which may itself be the chemotherapeutic drug) which has been radio-labeled, for example with a positron emitter, can provide external monitoring of drug accumulation in the tumor and/or normal host tissue by use of imaging technologies, for example with a PET scanner.

The present invention describes a method of labeling antitumor drugs with positron emitters, preferably the radioactive label $^{11}$C. The invention further describes the use of labeled antitumor drugs in the treatment of solid tumors. The invention is also a method of using labeled antitumor drugs to monitor the accumulation of drugs to solid tumors and to monitor modulators of cellular accumulation of drugs which act on mechanisms in the cancer cells of the tumors that prevent uptake and retention of drugs.

In one aspect, the invention is a method of measuring the accumulation of antitumor drugs by solid tumors comprising the following: administering an antitumor drug labeled with a positron-emitter to a patient having a solid tumor, and imaging at least part of the patient using PET. Typically, solid tumors include breast, lung, ovarian, gastrointestinal, prostate, sarcoma and head and neck tumors. The measurement of accumulation of the drug may be conducted either before or during a particular treatment regimen, and may be used to determine the efficacy of an antitumor drug for treating solid tumors; to measure the effectiveness of modulators of cellular accumulation including modulators of efflux and influx mechanisms; to measure the effectiveness of a combination of antitumor drugs where one or more of the drugs is labeled and the drugs are administered either simultaneously or sequentially; and for any other purpose for which measuring cellular accumulation of an antitumor would be beneficial. Exemplary drugs for use in the invention include $^{11}$C-paclitaxel, $^{11}$C-docetaxel, $^{11}$C-doxorubicin, $^{11}$C-epirubicin, $^{11}$C-topotecan, $^{11}$C-SN-38 and $^{11}$C-imatinib, although any drug for the treatment of solid tumors in radio-labeled form may be used.

In another aspect, the invention is a composition which is a radio-labeled drug. The invention includes: radio-labeled taxanes, for example $^{11}$C-paclitaxel and $^{11}$C-docetaxel; radio-labeled anthracyclines, for example $^{11}$C-doxorubicin and $^{11}$C-epirubicin; and other radio-labeled antitumor drugs, for example $^{11}$C-topotecan, $^{11}$C-SN-38 and $^{11}$C-imatinib. The invention is also a method of preparing a radio-labeled drug such as: radio-labeled taxanes, including $^{11}$C-paclitaxel and $^{11}$C-docetaxel; radio-labeled anthracyclines, including $^{11}$C-doxorubicin and $^{11}$C-epirubicin; and other radio-labeled antitumor drugs, including $^{11}$C- topotecan, $^{11}$C-SN-38 and $^{11}$C-imatinib.

The scope of this invention covers the preparation and diagnostic uses of antitumor drugs including paclitaxel, docetaxel, doxorubicin, epirubicin, topotecan, SN-38 and imatinib and others labeled with a positron emitter, preferably $^{11}$C. Based upon the images obtained, the likelihood of success for treatment of a patient's tumor with antitumor drugs can be predicted, as well as the utility of any modulators of drug delivery.

Further objectives and advantages will become apparent from a consideration of the description and examples.

DETAILED DESCRIPTION OF THE INVENTION

In describing embodiments of the present invention, specific terminology is employed for the sake of clarity. However, the invention is not intended to be limited to the specific terminology so selected. All references cited herein are incorporated by reference as if each had been individually incorporated.

The term "a" is intended to mean at least one unless the context indicates otherwise.

One goal of the present invention is to avoid exposing patients to toxic drugs that have no potential for benefit. The screening procedure of the present invention allows a rapid determination of whether a given tumor will be likely to respond to a particular drug. Such a rapid determination is important for other reasons, including the tendency of tumors to become refractory with time. Thus, immediate imaging with, for example, $^{11}$C-paclitaxel, $^{11}$C-docetaxel, $^{11}$C-doxorubicin, $^{11}$C-topotecan, $^{11}$C-SN-38, $^{11}$C-imatinib, $^{11}$C-epirubicin, or other radio-labeled antitumor drugs has the advantage of selecting patients with tumors that are likely to respond to therapy with the particular drug that is used. Further, the impact of various doses and schedules for delivery can be monitored in situ at the actual tumor under treatment conditions. This is important since levels of MDR and other modifiers of drug efficacy are often induced or altered during the course of therapy. It is within the scope of the present invention to re-test patients as often as therapeutically or diagnostically necessary to assess the changing efficacy of treatment.

The method of the present invention involves administration of tracer, nontoxic quantities of an antitumor drug that has been radio-labeled with a positron emitter. Imaging technologies such as a PET (Positron Emission Tomograph) scanner, can provide the ability to externally monitor drug delivery to the tumor and/or normal host tissue. This procedure is noninvasive and can be used in a prognostic sense, i.e., before a particular drug is administered in therapeutic quantities.

Drugs for use in the invention include docetaxel, paclitaxel, doxorubicin, epirubicin, topotecan, SN-38 and imatinib that have been radio-labeled with a positron emitter. Although a wide range of labeling techniques are known, for example replacing H with $^{18}$F, in exemplary embodiments, the radio-labeled drug is identical to the non-labeled drug except that it contains a radio-labeled atom. Thus, preferred radio-labeled drugs are those in which a naturally occurring atom is replaced with the same atom. As a particular example, $^{12}$C is replaced with $^{11}$C.

Others have used radio-labeled drugs to explore drug distribution in the body, but the present invention is useful in measuring drug accumulation in a tumor in order to make therapeutic decisions. For example, accumulation of a drug in a tumor may be measured to make predictions regarding effectiveness of the drug in a particular patient or against a particular tumor. Similarly, accumulation of an antitumor drug may be measured when the drug is co-administered with another antitumor drug or with a cellular accumulation modifier. The present invention measures drug accumulation regardless of the mechanism of drug delivery and regardless of any particular transport pump (influx or efflux) that may be operating.

Imaging Method According to the Invention

The present invention describes a method of visualizing antitumor drugs in the body. The drugs are first labeled by inserting a positron emitting isotope in the drug and then the drug is administered to a patient. The drug is labeled by replacing a normally occurring atom with a radioactive atom (e.g., $^{11}$C for $^{12}$C or $^{18}$F for $^{19}$F) in the drug structure. The antitumor drugs labeled with positron-emitting isotopes are then visualized by means of PET scan of the host's body. For the purpose of the present invention, a host includes any animal, preferably a human, to whom the positron emitting drugs of the present invention are administered for any therapeutic, diagnostic, prognostic, or experimental purpose.

The object of labeling antitumor drugs includes being able to determine and monitor the location of the drug in the body by imaging. For example, for taxane-type drugs, the invention may utilize $^{11}$C-paclitaxel or $^{11}$C-docetaxel. When cells accumulate antitumor drugs labeled with a positron-emitting isotope, the location of tissues comprising the cells can be determined by a PET scan.

According to the invention, a radio-labeled anti tumor drug can be administered simultaneously with the non-radio-labeled antitumor drug to customize treatment under the actual conditions of use. Radio-labeled drugs may also be administered in test quantities to determine the likelihood that the drug would be an effective therapeutic.

Significantly, many antitumor drug metabolites are rapidly excreted in the bile, so that circulating radioactivity would be primarily the parent molecule.

Need for Exact Match of Drug and Imaging Profile

Within the limits of the present understanding of antitumor drug pharmacology, only the radio-labeled versions of the drugs themselves can most reliably be used to predict accurately therapeutic drug delivery. The use of any other molecule, no matter how apparently similar, potentially compromises the quality of the whole concept.

For example, Li et al. have recently attempted to label paclitaxel with indium. Li C, Yu D F, Inoue T, Yang D J, et al. Synthesis, biodistribution and imaging properties of indium-111-DTPA-paclitaxel in mice bearing mammary tumors. *J. Nucl. Med.* 1997;38:1042–7. These investigators used Diethylenetriaminepentaacetic acid anhydride (DTPA), a chleating agent, to attach $^{111}$In to paclitaxel. The distribution in the body was found to be significantly different for the $^{111}$In-DTPA-paclitaxel than for the parent paclitaxel and was particularly affected by renal excretion. Because of these differences, it would require significant experimentation to characterize and correlate the properties of $^{111}$In-DTPA-paclitaxel with paclitaxel.

In addition to the above concerns, both $^{111}$In-DTPA and $^{99m}$Tc are inferior atoms for imaging compared with positron-emitters such as $^{11}$C and $^{18}$F. Unlike $^{111}$In-DTPA and $^{99m}$Tc, positron emitters ultimately generate two coincident photons, which greatly facilitates determination of the three-dimensional position within the body. The sensitivity of positron emitters such as $^{11}$C is considerably greater, which permits smaller tumors to be imaged.

In contrast to the substitution of non-radio-labeled atoms with radio-labeled atoms, attaching "extra" atoms to the drug, or changing some of the atoms in the drug, can create an unacceptable situation, in the absence of additional information. Using taxanes as an example, replacement of a hydrogen atom with longer-lived isotopes of fluorine or iodine has been attempted.

Ojima et al. report considerable differences in tumor cell sensitivity when fluorine analogs of docetaxel are evaluated, particularly at the 3'-C locus. Ojima I, Inoue T, Chakravarty S. Enantiopure fluorine-containing taxoids: potent anticancer agents and versatile probes for biomedical problems. *J. Fluorine Chem.* 1999; 97:3–10. Most importantly, the largest differences were observed for cell lines resistant to docetaxel. This variation in responsiveness might lead to some promising leads for alternative drug discovery. However, it would be misleading if the fluorinated molecule was used as a probe for decision-making regarding treatment with the parent docetaxel, because a favorable outcome would be projected in situations in which the tumor was actually resistant to docetaxel.

An iodinated version of paclitaxel has recently been proposed as a probe. John C S, Cole C E, Kiesewetter D O, Eckelman W C. Synthesis, characterization, in-vitro cell binding, and biodistribution of radioiodinated [125-I]-paclitaxel. *J. Nucl. Med.* 2000; 41:229P. Although limited biodistribution data were reported, no attempt was made to demonstrate that it was comparable to the parent paclitaxel molecule. In fact, the iodine was placed on the phenyl ring of the benzoyl group attached to the amino moiety at the 3'-C position of paclitaxel. This is the same portion of the molecule which produced variations for fluorinated analogs of docetaxel. It is also the major site of structural difference for docetaxel versus paclitaxel: substituting a tert-butyl group for the phenyl moiety.

Thus, considerable caution is required for any such modification. The burden of evidence that such a change is acceptable must be very high, particularly since the imaging information will be used to guide decisions about therapy of patients with life-threatening disease.

Further, the short half-life of $^{11}$C (20 minutes) is advantageous when compared to the 6 hour half-life for $^{99m}$Tc. Thus, multiple interventions may be conducted and probed in sequence during a single clinic day with $^{11}$C labeled drug, whereas $^{99m}$Tc labeled drug would be limited to one procedure per day, due to carryover of radioactivity from prior dosing. The shorter half-life of $^{11}$C also substantially reduces the biohazard, compared with $^{99m}$Tc, since most of the injected radio-activity would have left the patient before the patient left the clinic. Importantly, while expensive and extensive preclinical toxicology studies are usually required prior to human testing of a drug variant, none are required for positron-labeled version at a tracer dose of a currently-marketed drug. Radiodosimetry studies, of course, are still required.

In the case of taxanes, only paclitaxel and docetaxel are currently approved for therapeutic use. Other taxanes are under development, and might be approved and marketed in the future. If so, then these would also be candidates for PET imaging. Thus, nothing in this disclosure is intended to limit the application of these concepts solely to taxanes such as $^{11}$C-docetaxel or $^{11}$C-paclitaxel. Similarly, doxorubicin and epirubicin are the major anthracyclines for solid tumor therapy, but these concepts are not limited to $^{11}$C-doxorubicin or $^{11}$C-epirubicin. It is obvious to one skilled in the art that other classes of antitumor drugs may also be used in practicing the invention.

Assessment of Therapeutic Effects of Drugs on Particular Tumor Types

In an anticancer drug development program, the general strategy is to find the tumor types most likely to respond to a particular antitumor drug. Direct demonstration of clinical benefit is critical. Using typical methods, these definitive studies require hundreds or thousands of patients, which is resource-intensive and takes time. For example, it takes time to determine the success or failure in a general tumor type, and thus, to determine whether to continue investing money in clinical trials.

The present invention may be used to assess the likelihood of success in using a particular antitumor drug as a treatment for a particular type of tumor. According to the invention, a radio-labeled antitumor drug may be administered to patients having a particular tumor type. The accumulation of the radio-labeled drug in the tumors can be measured using the methods of the invention. Because analysis of drug accumulation in the tumor may be measured directly and results will not be dependent on measuring the long term response of patients, the number of patients required to conduct studies predicting drug effectiveness and the amount of time required to analyze the results may both be markedly reduced. In addition, the effects of modulators of cellular accumulation of drugs and the effectiveness of co-administration of more than one antitumor drug (as described below) may be addressed in the context of the broader patient population.

For example, imatinib is currently being tested for solid tumors other than CML and GIST, for which it is approved, and imaging could be an important marker for efficacy. The use of $^{11}$C-imatinib for imaging tumors may be especially significant for tumors located in the brain. Drug delivery to brain tumors is well known to be difficult, and could be readily assessed with $^{11}$C-imatinib. This is particularly important as high utilization of glucose by normal brain tissue precludes useful imaging of most brain tumors with compounds such as $^{18}$F-FDG.

Individualization of Therapy for Patients

Because there are multiple reasons for drug accumulation failures, a successful interventional strategy generally requires knowledge of the most important factor for each situation. However, administration of a drug labeled with a positron emitter allows for monitoring of the success of modulation to be determined non-invasively with external imaging techniques, if the radio-labeled agent is the same as the drug itself (e.g., paclitaxel), regardless of the mechanism(s) of drug delivery failure. Accordingly, if a tumor is known or suspected to be resistant to docetaxel, paclitaxel, doxorubicin, epirubicin, or another antitumor drug, imaging with a positron-labeled version of the drug can determine if the failure to respond is due to inadequate accumulation.

Recently, researchers have found that the MDR transporter is one of many transporters and other similar mechanisms, which prevent the accumulation of drugs in cells. For example, there are a large family of ATP-binding cassette (ABC) transporters, including MDR, MRP, and others. Expression of such transport mechanisms will vary from tumor-to-tumor. If accumulation of the drug is determined to be inadequate, possibly due to the presence of such systems, one course of action that is under intensive research is the search for strategies to improve drug accumulation in the tumor, potentially converting the situation from a failure to a treatment success.

Because it is known that the failure to accumulate drugs in the tumor in adequate amounts is a major cause for treatment failure, intensive research efforts are underway to improve drug delivery and/or retention. Modulators of cellular accumulation mechanisms are often discovered in the laboratory which increase the accumulation of antitumor drugs in tumor cells. The present invention allows rapid determination of the usefulness of such a modulator for specific patients with positron labeled antitumor drugs, by directly assessing whether drug accumulation is improved. Thus, the invention may be used to assess the impact of various modulators, doses, and schedules for accumulation in situ at the actual tumor to be treated.

Antitumor drugs have also been given intraperitoneally for treatment of ovarian carcinoma, with encouraging results. The ability to measure drug concentration at the tumor and/or normal tissue is critical to the evaluation of the success or failure of the therapy. Thus, the invention provides a means for directly assessing drug accumulation, a marked advantage over simply measuring plasma concentrations. Using the invention, it is thus possible to adjust therapy to fit a particular clinical situation. For example, the effect of drug uptake and retention modulators on drug delivery can be directly measured.

Assessment of Modulating Strategies

One of the major determinants of cellular accumulation is the operation of the efflux pumps. Many antitumor drugs may be effluxed from cells wherein MDR or other efflux pumps or transporters are highly expressed. The drugs are effluxed before they can accumulate. For example, taxanes may be prevented by efflux pumps from reaching their target, microtubules, and therefore do not bind to the microtubules. Thus, the presence of efflux transporters can prevent drugs from therapeutic action in the cell. Efflux transporters will also prevent accumulation of the radio-labeled antitumor drugs. In cells with highly expressed efflux mechanisms, antitumor drugs do not accumulate. The failure to accumulate antitumor drugs by tumor cells can indicate that high levels of efflux pumps are expressed in these cells and preventing therapeutic levels from being attained.

For commonly-used chemotherapy drugs such as taxanes, anthracyclines and vinca alkaloids, many tumor cells are resistant because they prevent accumulation of the drug in the cell. A common mechanism for this failure to accumulate a drug is the efflux pump MDR. In order to address these difficulties, modulators of cellular accumulation mechanisms (modulators) may be administered with an antitumor drug to increase drug accumulation in the tumor. By monitoring changes in accumulation when a modulator is added, the effectiveness of the modulator may be determined.

Other accumulation systems, for example, influx pumps or transporters, also exist and accumulation is the balance between influx and efflux rates. One skilled in the art will appreciate that similar principles apply to both efflux and influx systems. Thus, the present invention may be applied to influx pumps as well.

A variety of attempts to inhibit MDR have entered clinical testing, including dexverapamil, PSC833 from Novartis, LY335979 from Lilly, GG918 from Glaxo and VX-853 from Vertex. Some surfactants, such as the solvent Cremophor®, which is used in the intravenous formulation of Taxol®, have been reported to be modulators of paclitaxel uptake and retention by tumor cells. The present invention may be utilized to monitor the effectiveness of these and other cellular accumulation modulators, such as the modulation of efflux mechanisms by any modulator including use of excipients used in formulations of drugs.

Current clinical investigations of MDR modulators have only measured plasma concentrations of the drug itself. Since the purpose of modulation is to selectively improve accumulation of the drug to the tumor, the plasma data are not definitive. Because paclitaxel and docetaxel are substrates for MDR, studies directed towards clarifying uptake of these drugs by tumor cells would be clinically useful. Measurement of drug concentration in sequential biopsies of the tumor, with and without modulator, could provide more definitive comparisons, but are not practical in a clinical situation. However, according to the invention, radio-labeled taxanes, including $^{11}$C-paclitaxel or $^{11}$C-docetaxel, can be used to directly assess the success or failure of these MDR-modulating strategies at the tumor itself. Similarly, doxorubicin and epirubicin are substrates for multiple efflux pumps, so that determination of the accumulation of radio-labeled versions of these drugs, for example $^{11}$C-doxorubicin or C-epirubicin, would be clinically useful. The method according to the present invention utilizes positron-labeled antitumor drugs to measure the efficacy of MDR modulators of cancer cell efflux, influx, or other accumulation mechanisms.

The invention also envisions that substances which moderate or reduce efflux mechanisms could be co-administered with the radio-labeled antitumor drugs. Thus, it would be possible to determine an optimal dose of such a moderator that would allow therapeutic levels of antitumor drugs to accumulate in cells. Since the current list of known efflux pump moderators is quite low, and many are only known to work in cell-culture and not necessarily in vivo, the invention encompasses the use of labeled antitumor drugs as a research tool to find and explore other efflux moderators.

In addition to MDR, modulating strategies can be directed at other targets, including some which might be directed at decreasing normal host tissue concentrations as a way of reducing patient toxicity, rather than increasing tumor concentration. Overall, the same goal is sought: to increase selective action of the drug at the tumor site under conditions tolerable to the patient.

The present invention is useful in determining the level of impact of efflux type pumps or transporters on drug accumulation and thereby whether antitumor drugs are likely to be effective in the tumor imaged. When a radio-labeled antitumor drug is administered to a patient with a tumor with low drug accumulation, the tumors cannot be imaged by a PET scan, indicating that the tumor is unlikely to be effectively treated by the antitumor drug.

Assessment of Combination Chemotherapy Strategies

Often, when antitumor drugs are used therapeutically, maximal effects are achieved by co-administering more than one drug, such as the combination of a taxane with doxorubicin. The invention uses labeled antitumor drugs as a tool to determine optimal combinations of drugs that are co-administered. The determination of which drugs to co-administer will depend on the clinical circumstances of the disease to be treated. The decision of whether to co-administer a drug and which drug to use will depend on the clinical decision of the practitioner.

Although the combination of taxanes with doxorubicin is very promising, only plasma pharmacokinetics are currently accessible to assess therapeutic strategy Gianni, L. et al. Human pharmacokinetic characterization and in vitro study of the interaction between doxorubicin and paclitaxel in patients with breast cancer. *J. Clin. Oncol.* 15:1906–12, 1997; Gianni, L et al. Paclitaxel by 3-hour infusion in combination with bolus doxorubicin in women with untreated metastatic breast cancer: high antitumor efficacy and cardiac effects in a dose- and sequence-finding study. *J. Clin. Oncol.* 13:2688–2699, 1995.) An analogous set of clinical trials with docetaxel and various anthracyclines are underway. Sparano J A, O'Neill A, Schaefer P L, et al. Phase II trial of doxorubicin and docetaxel plus granulocyte colony-stimulating factor in metastatic breast cancer: Eastern Cooperative Oncology Group Study E1196. *J. Clin. Oncol.* 2000;18:2369–77. Assessing the accumulation of $^{11}$C-taxane can play a major role in dose and sequence decisions for these trials.

The present invention contemplates co-administration of radio-labeled antitumor drugs to determine efficacy of such combinations. Thus, using the imaging method of the invention, the effect of co-administration of more than one antitumor drug on drug accumulation may be determined. This determination may be made by assessing the accumulation of one or both of the antitumor drugs which are co-administered. The co-administration may be simultaneous or sequential. Accordingly, one or both of the co-administered antitumor drugs is labeled with a radio isotope and the accumulation of the radio-labeled drug at the tumor is measured using PET techniques.

Synthesis of Positron Emitting Antitumor Drugs

In another aspect, the invention relates to certain radio-labeled antitumor drugs useful in practicing the invention and methods of synthesizing radio-labeled drugs. For example, the invention is a method for synthesizing radiolabeled taxanes and anthracyclines. The invention is not limited to the specific drugs and methods of the examples, but include any equivalents to those compositions and procedures as would be suggested to one of skill in the art.

Taxanes

The invention includes compounds having the formula:

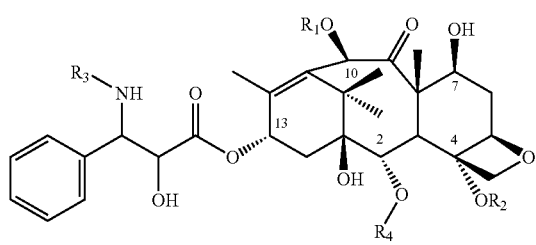

where $R_1$ is selected from the group consisting of H, acetate and $^{11}C$-acetate; $R_2$ is selected from the group of acetate and $^{11}C$-acetate; $R_3$ is selected from the group consisting of benzoyl, $^{11}C$-benzoyl and —$CO_2C(CH_3)_3$ and —$^{11}CO_2C(CH_3)_3$; $R_4$ is selected from the group consisting of benzoyl and $^{11}C$-benzoyl, and wherein the compound contains at least one atom of $^{11}C$. Radio-labeled paclitaxel and docetaxel are preferred taxanes. Radio-labeled paclitaxel may have a $^{11}C$ labeled acetate in the 4-position or the 10-position, or may have a radio-labeled benzoyl group at the $R_3$ amide or at $R_4$ in the 2-position. Radio-labeled docetaxel may have a radio-labeled tert-butyl carboxyl group at $R_3$, acetate at $R_2$ or benzoyl at $R_4$. Typically, the acyl groups are labeled at the carbonyl carbon.

The procedures for the synthesis of radio-labeled taxanes are modifications of those reported by Rao, K V et al. (Synthesis and evaluation of some 10-mono- and 2',10-diesters of 10-deacetylpaclitaxel. *J. Med. Chem.* 38:3411–14, 1990), and by Murray et al. in U.S. Pat. No. 5,808,113. The present methods utilize different reagents and reaction conditions as compared to these reports. The differences improve the efficiency of the reaction with respect to addition of $^{11}C$, e.g., via acetylation or benzoylation.

From the perspective of a large-scale manufacturing process, 10-deacetylpaclitaxel or the other taxane precursors are scarce and expensive resources, and the procedures are optimized for high yields of the taxane starting material. In this regard they are successful; e.g., Rao et al. report 85% conversion of 10-deactylpaclitaxel to paclitaxel. However, Rao et al. used approximately a 200-fold molar excess of acetyl donor. Based upon acetyl groups, the yield of this reaction would be 0.5%, which is impractical for radio-synthesis of an $^{11}C$-labeled PET probe. The present invention accomplishes the higher yields of 10–20% (based on acetyl donor) required to make PET imaging feasible. Thus, the present invention represents a major improvement over Rao et al. Using routine experimentation, a person skilled in the art may make minor alterations in the synthesis as may be required to adapt the conditions to those routinely used at their particular radiotracer facility.

Verification of the identify of the product is obtained by comparison with authentic nonradioactive reference material of paclitaxel (available commercially, e.g., from Sigma Chemical Company, Hauser Chemical Company, Hande-Tech Corporation) or docetaxel (available from Aventis/RPR). The final product, e.g., $^{11}C$-paclitaxel or $^{11}C$-docetaxel, is purified (e.g., using a solid-phase extraction cartridge) and prepared for intravenous injection in a suitable solvent (e.g., normal saline, Cremophor$^R$, ethanolic solution, Tween 80).

Similar methods may be useful for preparing other radio-labeled taxanes by incorporation $^{11}C$ into ester or carbamate substituents on the baccatin nucleus or side chains.

Anthracyclines

The invention also includes radio-labeled anthracyclines and particularly radio-labeled doxorubicin and epirubicin having the general formula:

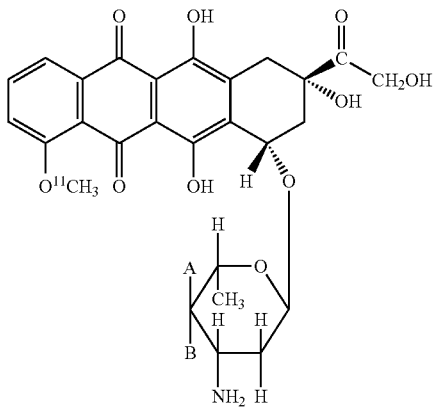

wherein one of A is H and B is OH ($^{11}C$-doxorubicin) or A is OH and B is H ($^{11}C$-epirubicin).

Due to the lack of commercial availability of a suitable anthracycline antitumor drug precursor for radiolabeling, several initial steps are required to generate a precursor for preparing radio-labeled doxorubicin and related drugs. In essence, after protecting the amine group in the sugar and the —OH groups, the methyl group at the 4-O-position is removed, producing a suitable precursor. Because these steps are performed prior to radiolabeling, high yield and rapid reactions are not essential. Radiolabeling of the precursor can be accomplished with $^{11}C$-methyl iodide, a standard radiolabeling reagent. Deprotection produces the desired radio-labeled product.

Other Antitumor Drugs

The invention also includes other radio-labeled antitumor drugs, for example, radio-labeled topotecan having the general formula:

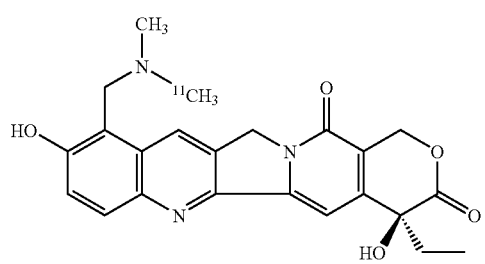

Radiolabeled topotecan may be prepared from N-desmethyl topotecan, which has been reported in the literature (Rosing H, Herben V M M, van Gortel-van Zomeren D M, et al., Isolation and structural confirmation of N-desmethyl topotecan, a metabolite of topotecan. *Cancer Chemotherapy and Pharmacology* 1997; 39:498–504), but is not commercially available. The N-desmethyl topotecan is prepared from commercial topotecan through a procedure adapted from the procedure of Rao, et al. (Rao, P. N., Acosta, C. K., Cessac, J. W., Bahr, M. L., Kim, H. K., Synthesis of N-desmethyl derivatives of 17 α-acetoxy-11β-(4-N,N-dimethylaminophenyl)-19-norpregna-4,9-diene-3,20-dione and mifepristone. *Steroids* 1999; 64:205–212). The $^{11}$C-topotecan is prepared from N-desmethyl topotecan by methylation with $^{11}$C-methyl iodide.

Another potentially useful radio-labeled drug for use in practicing the invention is $^{11}$C-mitoxantrone. Current efforts for preparing this drug by placing a $^{11}$C-label in one of the hydroxyethyl groups have not been successful.

Radiolabeled SN-38 may be prepared from labeled n-propionaldehyde and 10-hydroxycamptothecan using a published method (Sawada S, Okajima S, Aiyama R, Nokata K, Furuta T, Yokokura T, Sugino E, Yamaguchi K, Miyasaka T. Synthesis and antitumor activity of 20(S)-camptothecin derivatives: carbamate-linked, water-soluble derivatives of 7-ethyl-10-hydroxycampothecin. *Chem. Pharm. Bull. (Tokyo)* 1991; 39:1446–50) that is adapted for small-scale synthesis and rapid reaction time. The product can be isolated and purified by solid-phase extraction and HPLC, with LC-MS characterization. Yields of labeled SN-38 can be approximately 25%, based upon propionaldehyde. Under these conditions, the reaction was successfully conducted using labeled propionaldehyde prepared from either trideuterated methyl iodide or pentadeuterated ethyl iodide or $^{14}$C-methyl iodide. The potential precursors for donors in position labeling, $^{11}$C-methyl iodide and $^{11}$C-ethyl iodide, are universal reagents in PET chemistry labs, and the unlabeled precursor, 10-hydroxycamptothecan, is commercially available.

Radiolabeled imatinib is prepared by methylation of N-demethyl imatinib, which is itself prepared from pharmaceutical grade commercial imatinib by modification of a method described for demethylation of the alkaloid galanthamine. Mary A, Zafiarisoa R, Ouillou C, and Thal C; Selective N-demethylation of galanthamine to norgalanthamine via a non-classical Polonovski reaction. *Tetrahedron Letters* 1997; 38: 5151–5152. N-demethyl imatinib is reacted with labeled methyl iodide, purified using HPLC and characterization by LC-MS. Under these conditions, the reaction can be conducted with either trideuterated methyl iodide or $^{14}$C-methyl iodide, in yields of approximately 40%, based upon methyl iodide. The very short reaction time, mild reaction conditions, lack of requirements for protecting groups, and small amounts of material, combined with reliable and reasonable yields, make this scheme ideal for use in PET chemistry. The donor for positron labeling, $^{11}$C-methyl iodide, is a universal reagent in PET chemistry labs.

EXAMPLES

Example 1

Synthesis of $^{11}$C-paclitaxel

10-Deacetylpaclitaxel (6 mg) (commercially available) in pyridine (0.5 ml) was reacted with chlorotriethylsilane (0.1 ml) for 1 hour at 60° C. to yield 7,2'-di-(triethylsilyl)--10-deacetylpaclitaxel. This molecule is the immediate precursor for radiolabeling; it is stable at room temperature and can be stored until needed.

To a solution of (50 µg, 60 nmol) of 7,2'-di-(triethylsilyl)-10-deacetylpaclitaxel, was added dimethylaminopyridine solution (90µl of 300 mg/ml in methylene chloride), and of tert-butyl diphenyl chlorosilane (20 µL). Acetyl chloride (10 µl of a 1:5000 solution in methylene chloride, 25 nmol) was then added and the mixture heated to 105° C. for 10 minutes. The silyl groups were removed within 2 minutes by adding methylene chloride (400 µl) and tetrabutylammonium fluoride solution (50 µl of 1 M solution in tetrahydrofuran). Verification of the identify of the product via HPLC and mass spectrometry was obtained by comparison with authentic reference material of paclitaxel (available commercially). The overall yield, based upon the acetyl donor, was 10–20%.

This procedure works with sufficient yield (10–20% overall), in the required time limit (15 minutes from addition of acetyl chloride until beginning of clean-up), and with small quantities of material (e.g., 50 µg). Thus, $^{11}$C-paclitaxel may be prepared simply by substituting $^{11}$C-acetyl chloride for unlabeled acetyl chloride.

On the day of use, $^{11}$C is prepared by a cyclotron in the form of $^{11}$C-CO$_2$. This radio-labeled carbon dioxide is rapidly converted to $^{11}$C-acetyl chloride using published procedures. Luthra S K, Pke V W, Brady F. Preparation of some NCA [1–11-C] acid chlorides as labeling agents. *Appl. Radiat. Isot.* 1990; 41:471–6. The final product, $^{11}$C-paclitaxel, is purified (e.g., using a solid-phase extraction cartridge or HPLC) and prepared for intravenous injection in a suitable solvent (e.g., normal saline, Cremophor$^R$ or ethanolic solutions).

Example 2

Alternative Synthesis of $^{11}$C-paclitaxel

Benzoyl chloride (8 µl of 1:1000 dilution in acetonitrile) is added to a solution of paclitaxel primary amine (50 µg) (commercially-available) in acetonitrile (200 µl). After 2 minutes at room temperature, 60% recovery of product was obtained.

Conversion of this procedure to radio-synthesis requires preparation of $^{11}$C-benzoyl chloride, which is known in the art by following typical Gringard reaction schemes. Mathews W B, Burns H D, Danals R F, Rabert H T, Naylor E M. Carbon-11 labeling of a potent, nonpeptide, AT1-selective angiotensin-11 receptor antagonist, MK-996. *J. Labelled Compounds and Radiopharmaceuticals* 1995; XXXVI:729–37. For $^{11}$C-paclitaxel, purification may be accomplished by HPLC or by adding acidic water and methylene chloride.

Example 3

Synthesis of $^{11}$C-docetaxel

Preparation of Docetaxel Primary Amine

The starting material for the preparation of $^{11}$C-docetaxel is docetaxel primary amine, which is not available commercially. The free amine is prepared by removal of the tert-butyl carbonyl group from docetaxel using formic acid or other methods known in the art.

Docetaxel was purified from its commercial form (TAXOTERE® for Injection RhonePoulencRorer) by silica gel chromatography. Docetaxel (4.5 mg) was dissolved in EtOH (1 ml). After addition of formic acid (1 ml) the mixture was stirred at room temperature for 10 days. Overall conversion to docetaxel primary amine was 48%. Water (2 ml) and methylene chloride (2 ml) were added to the reaction solution and mixed. The aqueous phase containing docetaxel primary amine was separated from the organic phase containing residual docetaxel. The aqueous phase was neutralized with saturated sodium bicarbonate in water. Methylene chloride (12 ml) was added to the aqueous component, mixed and centrifuged. The organic phase, which contained the docetaxel primary amine, was separated and dried with a gentle stream of air at 55° C.

Preparation of $^{11}$C-docetaxel

Docetaxel primary amine (100 μg) was dissolved in ethyl acetate (200 μl) and 0.6 equivalents of di-tert butyl dicarbonate (di-BOC) was added. The solution was heated at about 60° C. for 10 minutes. The docetaxel product was produced in 15% yield and its identity verified by HPLC.

This rapid, single-step process for preparation of unlabeled docetaxel may be converted to a radioactive method by the use of $^{11}$C-labelled di-BOC. The key step is substitution of $^{11}$C—$CO_2$ for unlabeled $CO_2$. Preparation of di-tert-butyl dicarbonate is described in several publications, including: U.S. Pat. No. 5,151,542, entitled, "Process For Preparing Di-Tert-Butyl Dicarbonate" or U.S. Pat. No. 5,162,565, entitled, "Process For Preparing Ditertiary-Alkyl Dicarbonate".

Example 4

Alternative Synthesis of $^{11}$C-docetaxel

In a two-step procedure, 10-acetyldocetaxel is prepared from the paclitaxel primary amine, followed by 10-deacetylation via hydrogen peroxide to yield docetaxel. Paclitaxel primary amine (0.5 mg) was added to ethyl acetate (0.2 ml) containing an equimolar amount of di-tert butyl dicarbonate. The solution was heated at 65° C. for 30 minutes to form 10-acetyl docetaxel. Upon heating at 125° for about 6 minutes, 20% conversion of 10-acetyl-docetaxel to docetaxel was obtained in 15% hydrogen peroxide.

As in the preceding example, conversion of this procedure to radio-synthesis requires preparation of $^{11}$C-labeled di-BOC.

Example 5

Synthesis of $^{11}$C-doxorubicin

Preparation of Protected Demethylated Doxorubicin

Protected demethylated doxorubicin, the precursor for the synthesis of radio-labeled doxorubicin, was formed by first dissolving doxorubicin (20 mg, 36 μmol) in isopropanol (5 ml) and sodium borate (1 ml of 0.25M), and reaction with 9-fluorenylmethyl chloroformate (fmoc) (20 mg, 70 μmol) at room temperature with sonication for 20 min. The solution was reduced in volume under a stream of air to ~1 ml, extracted into chloroform, and washed with water (2×). The chloroform was removed under a stream of air, leaving dox-fmoc suitable for the next step.

Dox-fmoc (10 mg) was dissolved in dry pyridine (3 ml) and cooled in an ice bath. Benzoyl chloride (125 μl, 0.9 mmol) was slowly added, and allowed to react for 30 min. The reaction (monitored by HPLC) was quenched by addition of water (0.5 ml), and blown down under air (50° C.). The reaction mixture was extracted into methylene chloride and washed with water (3×). The methylene chloride was removed under a stream of air, and dried under vacuum, producing dox-fmoc-4bz as identified by HPLC-MS.

Dox-fmoc-4bz was dissolved in methylene chloride (about 4 ml) and cooled in a dry ice/isopropanol bath. $BCl_3$ (100–200 μl of 2M in heptane) was added. The reaction was maintained at −78° C. for about 2 hours (monitored by LC), and quenched by addition of 2% acetic acid (1 ml) at −78° C., washed with water (2×), and the methylene chloride removed under a stream of air, and dried under vacuum. The 4-OH-dox-fmoc-4bz product was isolated by HPLC, in about 5% yield.

Synthesis of $^{11}$C-Doxorubicin

Methylation conditions were adapted from Bernardi et al. Bernardi L, Masi P, Spaini O, Suarato A, Arcamone F. 4-Demthoxy-4-alkoxydaunorubicins. Il Farmaco Ed. Sc. 1978; 34:884–889. The 4-OH precursor (4-OH-dox-fmoc-4bz) was added to a vial containing AgO (approximately 3 mg) and isopropanol (250 μl). Methyl iodide (10 ug, 75 nmol) was introduced, the vial was capped and heated at 120° C. for about 13 minutes. The reaction mixture was filtered and dried under a stream of air. The protecting groups were removed stepwise, adapting the procedures of Adams. Adams N, Blake C, Broadhurst M J et al. Synthesis and antitumor activity of novel 4-demethoxyanthracyclines. J. Med. Chem. 1990; 33:2375–9. The dry reaction products were dissolved in acetone to which 0.5 volumes of dilute KOH is added, heated to 100° C. for about 6 minutes, then neutralized with dilute acetic acid and dried. The reaction products were then redissolved in chloroform and treated with morpholine at 100° C. for 5 minutes. Doxorubicin can then be isolated by HPLC.

Radio-labeled doxorubicin is prepared by substituting $^{11}$C-methyl iodide for the nonradioactive methyl iodide in the methylation step. One skilled in the art will appreciate that the reaction has been conducted on a scale and with amounts of reagents in the range and within a timeframe suitable for tracer radio labeling with $^{11}$C-methyl iodide. Preparation of $^{11}$C-methyl iodide is established in the art and a standard reagent at facilities equipped for PET synthesis.

$^{11}$C-epirubicin may be prepared in an identical manner by substitution of epirubicin for doxorubicin.

Example 6

Synthesis of $^{11}$C-topotecan

Synthesis of the N-desmethyl topotecan.

The starting material for the preparation of $^{11}$C-topotecan, N-desmethyl topotecan, is not commercially available. The N-desmethyl topotecan was prepared from commercial topotecan through a procedure adapted from the procedure of Rao, et al. (Rao, P. N., Acosta, C. K., Cessac, J. W., Bahr, M. L., Kim, H. K. Synthesis of N-desmethyl derivatives of 17α-acetoxy-11β-(4-N,N-dimethylaminophenyl)-19-norpregna-4,9-diene-3,20-dione and mifepristone. Steroids 1999; 64:205–212.)

To a solution of Topotecan dissolved in 2:1 tetrahydrofuan:methanol (v:v) was added approximately 20 mol eq. CaO, and cooled in an ice bath. $I_2$ (10 mol eq.) was added. The reaction was allowed to proceed for 2 hours with periodic vortexing. The reaction was quenched with 10% sodium thiosulfate, acidified with dilute formic acid, the solids removed by centrifugation, and dried. N-Desmethyl topotecan was purified by HPLC. Identity of the N-desmethyl topotecan was confirmed by LC/MS.

Preparation of $^{11}$C-Topotecan

N-desmethyl topotecan was dissolved in dimethylforamide to which methyl iodide was added. The reaction vessel was capped and heated at 100° C., for about 4 minutes. The reaction mixture was concentrated and $^{11}$C-topotecan purified by HPLC.

Radio-labeled topotecan is prepared by substituting $^{11}$C-methyl iodide for nonradioactive methyl iodide. Preparation of $^{11}$C-methyl iodide is established in the art and a standard reagent at facilities equipped for PET syntheses.

Example 7

Synthesis of $^{11}$C-SN-38

Preparation of Labeled N-propionaldehyde
The donor for the label, n-propionaldehyde, was prepared via several methods:

Example 7a

[$^{11}$C]ethyl iodide is a PET reagent known to the art (e.g., Ishiwate K., Ishii S-I, Shinoda M, Mackawa S, and Senda M, Automated synthesis of radiochemically pure $^{11}$C-labeled ethyl, propyl, and butyl iodides. *Appl. Radiation and Isotopes,* 1999; Vol. 50, pp 693–697). In order that structural verification could be obtained, deuterated ethyl iodide ($d_5$-ethyl iodide) was used as the labeled donor in the following procedure. n-Butyl lithium (100 µl of 1.6 M in hexane) was added to 5 ml dry diethyl ether at −78° C. After 1 min. $d_5$-ethyl iodide was added. Dry $CO_2$ was bubbled into the mixture. The sample was maintained at 60° C. for 3 min. Lithium aluminum hydride (0.25 ml of 1 M in diethyl ether) was added. After 3 min. saturated NaCl (5 ml) was added. The ether layer was collected and dried by passage through a $Na_2SO_4$ column. The ether was evaporated and n-propanol was oxidized to n-propionaldehyde with a solution of pyridinium chlorochromate in toluene at 40° C. The n-propionaldehyde was then coupled to the precursor as above to form $d_5$-SN-38. The successful synthesis of $d_5$-SN-38 was confirmed by LC-MS.

Example 7b

Methyl lithium, MeLi, is a suitable intermediate for the synthesis of propionaldehyde when prepared from methyl iodide according to Reiffers et al., 1980, *Int. J. Appl. Radiat. Isot.* 31 535, 1423. MeLi was added to a solution of thienyl cuprate in THF at −78° C. and allowed to react for 5 min. The solution was then warmed to 0° C., and ethylene oxide (~10 ml) was bubbled into the solution to form n-propanol, which was oxidized to n-propionaldehyde as described above.

Example 7c

Propionaldehyde was produced from methyl magnesium iodide. Labeled methyl magnesium iodide (deuterated) was reacted with Cu in dry ether. Ethylene oxide (~10 ml) was then slowly bubbled into the reaction vessel. The resulting n-propanol (after hydrolysis) was oxidized to n-propionaldehyde as above. Elsinga et al., (Synthesis of [$^{11}$C]methyl magnesium iodide and its application of the introduction of [$^{11}$C]-N-tert-butyl groups and [$^{11}$C]-sec-alcohols, *Appl. Radiat. Isot.*, Vol. 46 pp. 227–231, 1995) have reported the synthesis of $^{11}$C-methyl magnesium iodide from $^{11}$C-methyl iodide.

Synthesis of $^{11}$C-SN-38
For the coupling of the labeled propionaldehyde to the precursor, the published method of Sawada et al. was adapted for small-scale synthesis. Sawada S, Okajima S, Aiyama R, Nokata K, Furuta T, Yokokura T, Sugino E, Yamaguchi K, Miyasaka T. Synthesis and antitumor activity of 20(S)-camptothecin derivatives: carbamate-linked, water-soluble derivatives of 7-ethyl-10-hydroxycamptothecin. *Chem. Pharm. Bull.* (*Tokyo*) 1991; 39:1446–50). Labeled n-propionaldehyde was introduced to a solution of the commercially available 10-hydroxycamptothecan (250 µg) in 10% $H_2SO_4$. $FeSO_4.7H_2O$ (4 mg) was added and allowed to react for 4 minutes. $H_2O_2$ (150 µg) was added to complete the coupling. The product was isolated and purified by solid-phase extraction and HPLC, with LC-MS characterization. The yield of labeled SN-38 was approximately 25%, based on propionaldehyde.

Example 8

Synthesis of $^{11}$C-Imatinib

Synthesis of N-demethyl imatinib
The precursor for synthesis labeled imatinib, N-demethyl imatinib, was prepared from commercially available pharmaceutical grade imatinib by modification of a method described for demethylation of the alkaloid galanthamine. (See, Mary A, Zafiarisoa R, Ouillou C, and Thal C; Selective N-demethylation of galanthamine to norgalanthamine via a non classical Polonovski reaction. *Tetrahedron Letters* 1997; 38: 5151–5152). Imatinib was reacted with 2 equivalents of 3-chloroperoxybenzoic acid in dichloromethane at room temperature for 3 hours. The intermediate N-oxygenated species was treated with 4 equivalents of $FeSO_4.7H_2O$ in methanol at 4° C. for 2 hours. The resultant N-demethyl imatinib was purified by HPLC and characterized by LC-MS.

Synthesis of $^{11}$C-Imatinib
N-demethyl imatinib (approximately 100 µg) was dissolved in DMSO (200 µl) to which was added $K_2CO_3$ (2 µl of 0.2 M). Labeled methyl iodide (4 µg in toluene) was added, and allowed to react for 8 minutes at 80° C. The solvent was removed, the residue was dissolved in mobile phase, purified by injection onto a HPLC, and characterized by LC-MS. Under these conditions, the reaction was successfully conducted with either trideuterated methyl iodide or $^{14}$C-methyl iodide, in yields of approximately 40%, based upon methyl iodide.

Example 9

General Procedures for Clinical Use

The positron-labeled antitumor drug is prepared shortly before use, i.e., within 2 hours of injection, and preferably within less than 1 hour. The positron-labeled antitumor drug with an activity of 1 to 300 mCi, preferably 10–60 mCi, is injected into the patient as an intravenous bolus, i.e., within less than 5 minutes, preferably in 1 minute. The patient is placed in a PET scanner, and images are obtained using standard techniques known to the art at 5- to 10-minute intervals following the injection, up to at least 60 minutes, preferably 90 minutes, when image quality is satisfactory. When $^{18}$F or other positron-emitting isotopes with a longer half-life is used, imaging for hours or a day or more may be feasible. Variations and improvements in machine technology may permit even longer imaging periods, which is desirable. It is within the scope of the present invention for an operator skilled in the art of PET scanning to modify the method in such ways as changes and improvements in PET scans require or allow.

Example 10

Use of Positron-Labeled Antitumor Drugs for Selection of Chemotherapy

A patient with a tumor is imaged with one or more positron-labeled antitumor drugs according to the procedures in Example 9. One or more of the labeled drugs is injected. If more than one antitumor drug is used, a 90 minute period (or longer) between injections is necessary for $^{11}$C labeled drugs. Four or more hours between separate injections may be required if $^{18}$F or other isotopes with longer half-lives are used. Based upon the accumulation of antitumor drug demonstrated in the images, therapy can be guided by whether the patient's tumor is classified as sensitive or resistant to one or more of the drugs.

Example 11

Development of Modulators for Antitumor Drug Delivery to Tumors

The procedures in Example 9 can be used to obtain a baseline evaluation of antitumor drug accumulation within the tumor, in the absence of any modulation attempts. These procedures are then repeated in the presence of a specific modulation strategy, or a series of modulation attempts, and the images are compared to determine success or failure.

Example 12

Combinations of Antitumor Drugs

The procedures used in Example 9 may be used to monitor antitumor drug accumulation in both normal tissue and tumors when combinations of antitumor drugs are used under a variety of dose and temporal adjustments. In practicing the method, one of the antitumor drugs is labeled in order to determine the effect of other antitumor drugs on the delivery of the labeled drug. Alternatively, if the drugs are administered sequentially and non-simultaneously, both of the antitumor drugs of the combination may be labeled in order to determine drug delivery overall.

Example 13

Targeting of Tumor Types for Drug Development

The use of positron-labeled antitumor drugs, following the procedures of Example 9, provide a basis for selecting tumor types for further emphasis in drug development. Indeed, the entire paradigm of drug selection could shift from dominance by histopathologic findings to reliance upon actual accumulation of radio-labeled antitumor drugs to guide initial therapy.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method of measuring the accumulation of antitumor drugs by solid tumors comprising:
   administering an antitumor drug labeled with a positron-emitter to a patient having a solid tumor; and,
   imaging at least part of the patient using PET,
   wherein the antitumor drug is a camptothecin analog or derivative.

2. The method according to claim 1, wherein the solid tumor is selected from the group consisting of breast, lung, ovarian, gastrointestinal, prostate, sarcoma and head and neck tumors.

3. The method of claim 1, wherein the labeled drug is at least one drug selected from the group consisting of $^{11}$C-topotecan, and $^{11}$C-SN-38.

4. A method of determining the efficacy of an antitumor drug for treating solid tumors comprising:
   administering an antitumor drug labeled with a positron-emitter to a patient having a solid tumor; and,
   imaging at least part of the patient by PET to measure accumulation of the labeled antitumor drug,
   wherein the antitumor drug is a camptothecin analog or derivative.

5. The method according to claim 4, wherein the labeled antitumor drug is administered prior to a course of treatment of the patent.

6. The method of claim 4, wherein the labeled antitumor drug is administered during the course of treatment of the patent.

7. The method of claim 4, wherein the labeled drug is at least one drug selected from the group consisting of $^{11}$C-topotecan, and $^{11}$C-SN-38.

8. A method of measuring the effectiveness of modulators of cellular accumulation mechanisms in tumors comprising:
   administering an antitumor drug labeled with a positron-emitter to a patient;
   administering a modulator to the patient; and,
   imaging at least part of the patient by PET to measure accumulation of the labeled antitumor drug,
   wherein the antitumor drug is a camptothecin analog or derivative.

9. The method of claim 8, wherein the accumulation of labeled antitumor drug is measured before and after administering the modulator to the patient and the levels of antitumor drug accumulation before and after administering the modulator are compared.

10. The method of claim 8, wherein the modulator affects an efflux mechanism.

11. The method of claim 8, wherein the modulator affects an influx mechanism.

12. The method of claim 8, wherein the labeled drug is at least one drug selected from the group consisting of $^{11}$C-topotecan, and $^{11}$C-SN-38.

13. A method for measuring the effectiveness of a combination of antitumor drugs comprising:
    administering more than one antitumor drug to a patient having a solid tumor, wherein at least one of said antitumor drugs is labeled with a positron-emitter; and,
    imaging at least part of the patient by PET to measure accumulation of the labeled antitumor drug,
    wherein the at least one antitumor drug labeled with a positron-emitter is a camptothecin analog or derivative.

14. The method of claim 13, wherein two antitumor drugs are administered to the patient.

15. The method of claim 13, wherein one of said antitumor drugs is labeled with a positron-emitter.

16. The method of claim 13, wherein two of said antitumor drugs are each labeled with a positron-emitter.

17. The method of claim 13, wherein a first antitumor drug and a second antitumor drug are administered simultaneously.

18. The method of claim 13, wherein a first antitumor drug and a second antitumor drug are administered sequentially.

19. The method of claim 13, wherein the labeled drug is at least one drug selected from the group consisting of $^{11}$C-topotecan, and $^{11}$C-SN-38.

20. A compound having the formula:

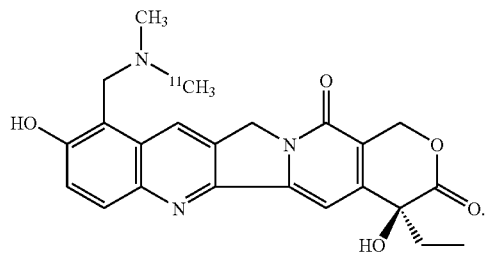

21. A method of synthesizing the compound according to claim 20, comprising the step of reacting N-desmethyl topotecan with $^{11}$C-methyl iodide to produce $^{11}$C-topotecan.

22. A compound having the formula:

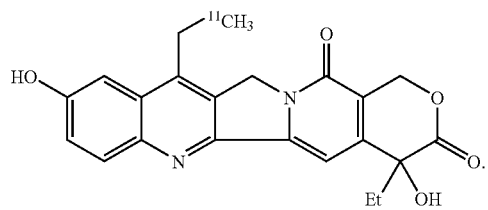

23. A method of synthesizing the compound according to claim 22, comprising the steps of:
reacting HC(O)CH$_2$—$^{11}$CH$_3$ with 10-hydroxycamptothecan;
reacting the resultant mixture with hydrogen peroxide; and,
isolating

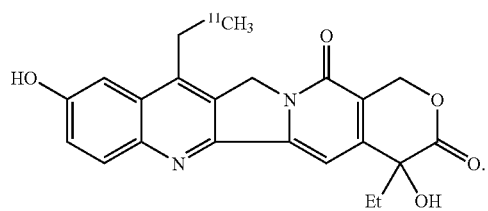

* * * * *